United States Patent [19]

Doresey, III

[11] Patent Number: 5,261,905
[45] Date of Patent: Nov. 16, 1993

[54] SPATULA-HOOK INSTRUMENT FOR LAPAROSCOPIC CHOLECYSTECTOMY

[76] Inventor: James H. Doresey, III, 2117 NE. 44th St., Lighthouse Point, Fla. 33064

[21] Appl. No.: 940,636

[22] Filed: Sep. 4, 1992

[51] Int. Cl.⁵ .............................................. A61B 17/39
[52] U.S. Cl. ........................................ 606/45; 606/49; 606/41
[58] Field of Search ................. 606/37, 39, 40, 41, 606/42, 43, 44, 45, 46, 47, 48, 49, 50, 51

[56] References Cited

U.S. PATENT DOCUMENTS

| | | | |
|---|---|---|---|
| 1,945,327 | 1/1934 | Morse | 606/49 |
| 4,517,974 | 5/1985 | Tanner | 606/16 |
| 4,593,691 | 6/1986 | Lindstrom et al. | 606/45 |
| 4,674,499 | 6/1987 | Pao | 606/50 |
| 4,943,290 | 7/1990 | Rexroth et al. | 606/49 |

FOREIGN PATENT DOCUMENTS 2160102 12/1985 United Kingdom ................ 606/45

Primary Examiner—Stephen C. Pellegrino
Assistant Examiner—Sonya C. Harris
Attorney, Agent, or Firm—Malin, Haley, DiMaggio & Crosby

[57] ABSTRACT

An improved electro-surgical laparoscopic cholecystectomy instrument having a housing (12) formed from an elongated rigid tube for suction and irrigation functionality wherein a distal end (16) of the housing (12) is placed an electrode (18) in the shape of a spatula with an arcuate placed notch (28) therein. The tip (30) of the spatula facilitates the blunt dissection at the electrode (18) and the notch allows for retracting dissection. The electrode (18) available to accept the requisite energy of electrocautery for coagulating and cauterizing.

9 Claims, 2 Drawing Sheets

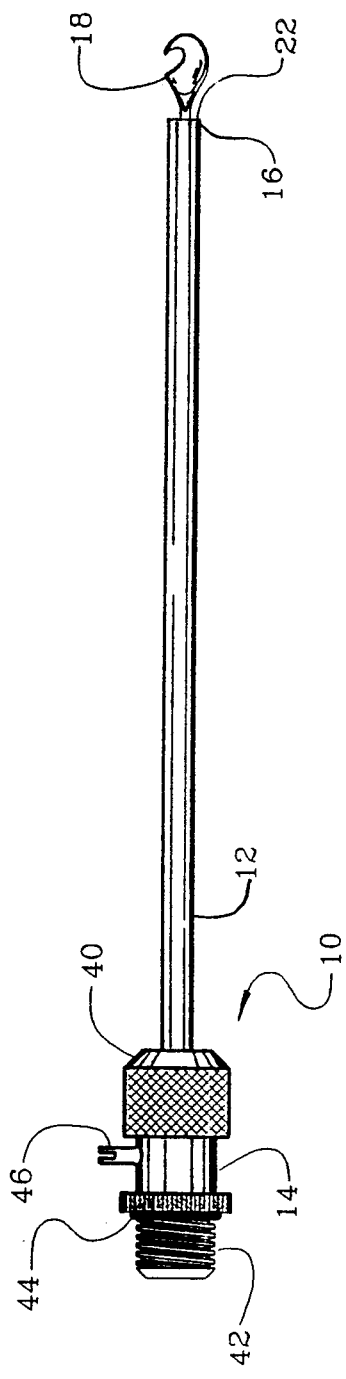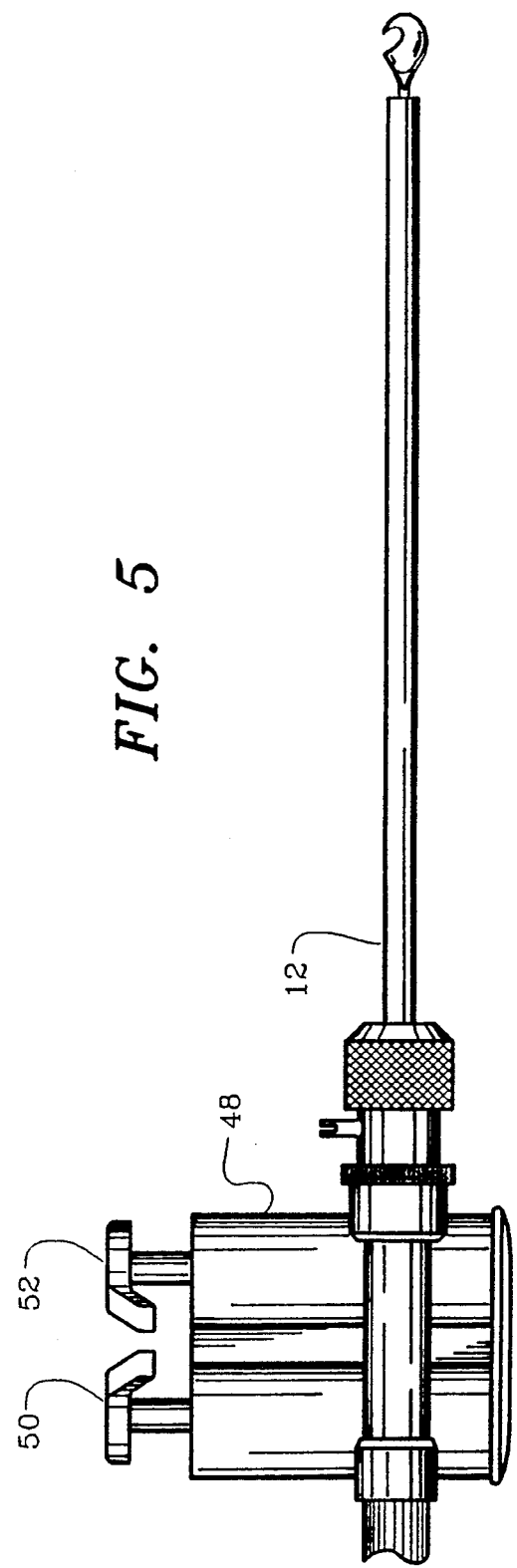

SPATULA-HOOK INSTRUMENT FOR LAPAROSCOPIC CHOLECYSTECTOMY

BACKGROUND OF THE INVENTION

I. Field of the Invention

This invention relates generally to electro-surgical instruments, and more particularly, to a combination spatula and hook instrument for laparoscopic cholecystectomy.

II. Description of the Prior Art

Treatment of diseased gallbladders can be performed by a number of methods, cholecystectomy being a conclusive act. Conventional removal of the gallbladder requires a moderately large abdominal incision. The gallbladder is normally removed by blunt dissection of the gallbladder from the liver bed via electro surgery techniques. Once released, the dissected gallbladder can be easily removed through the incision.

More recently, the method of laparoscopic cholecystectomy has revolutionized the surgery procedure by eliminating the large abdominal incision previously required. The result is that gallbladder surgery can be performed on a near out-patient mode requiring only small incisions be made in the umbilicus, lower and upper abdomen. A trocar is inserted into the umbilicus incision with a removable stylet to provide for insertion of a laparoscope allowing viewing on a video screen.

The remaining incisions are made for insertion of cannulas used to permit surgical instruments to be inserted therethrough. There are several electro-surgical instruments that are predominantly utilized during the electro-surgical dissection. One of the most popular instruments is a spatula shaped like a small spoon. The spatula design is ideal for conforming to the gallbladder bed and bluntly dissecting the gallbladder from the liver. The tip has a long neck that extends past the insulation located at the end of a cannula. A second popular instrument is a wire attached to the end of a cannula that is formed into the shape of a J-hook or L-hook. Applying energy through the surgical tool allows tissue cutting and assists in coagulation and cauterizing by heating of the contacted tissues.

The problem with the prior art is that the spatula or the hook is normally selected via immediate need or physician preference. Both instrument designs have their advantages yet can not simultaneously be utilized. Each instrument must be removed and the required instrument is inserted as needed. For instance, if the hook instrument is required and the spatula instrument is currently inserted, the spatula instrument must be removed before insertion of the hook instrument. This exchange results in a loss in time and increases the cost.

Therefore, there exists a need for a single instrument capable of performing the requirements of the spatula instrument and hook instrument.

SUMMARY OF THE INVENTION

The present invention provides an improved electro-surgical instrument for use in laparoscopic cholecystectomy by use of a housing formed from an elongated stainless steel and TEFLON insulation covered tube that has a length and a diameter for slidable insertion into and extension through a conventional cannula. The tube is hollow allowing both suction and irrigation functionality when attached to the appropriate supply device such as a vacuum source and/or irrigation device. The base end of the device is particularly adaptable to the NEZHAT-DORSEY HYDRO-DISSECTION ("NDHD") Trumpet Valve. At a distal end of the housing is placed a spatula with an arcuate notch, the combination of which facilitates the blunt dissection at the tip of the electrode and allows for retracting dissection by use of the notch. The length of the housing permits the electrode to reach the gallbladder when the instrument is inserted through the cannula. The electrode is available to accept the requisite heat energy of electrocautery for coagulating and cauterizing.

In accordance with the present invention, it is an object thereof to provide a dual purpose laparoscopic cholecystectomy instrument that is insertable though a cannula for use in dissection of the gallbladder from the liver.

Yet still another object of the invention is provide an improved electro-surgical instrument that is shaped in such a manner so as to facilitate the blunt dissection at the tip and also the retracting dissection by means of a notch placed in the perimeter surface of the instrument.

Still another object of the invention is to provide an improved electro-surgical instrument acceptable to the requisite heat energy for electrocautery for coagulating and cauterizing.

In accordance with these and other objects which will become apparent hereinafter, the instant invention will now be described with particular reference to the accompanying drawings.

BRIEF DESCRIPTION OF THE DRAWINGS

FIG. 4 is a perspective view of the instant invention illustrating the base end conductor with vacuum/irrigation coupling; and FIG. 5 is a perspective view of the instant invention coupled to an NDHD Trumpet Valve.

DETAILED DESCRIPTION OF THE PREFERRED EMBODIMENT

Figure 1:
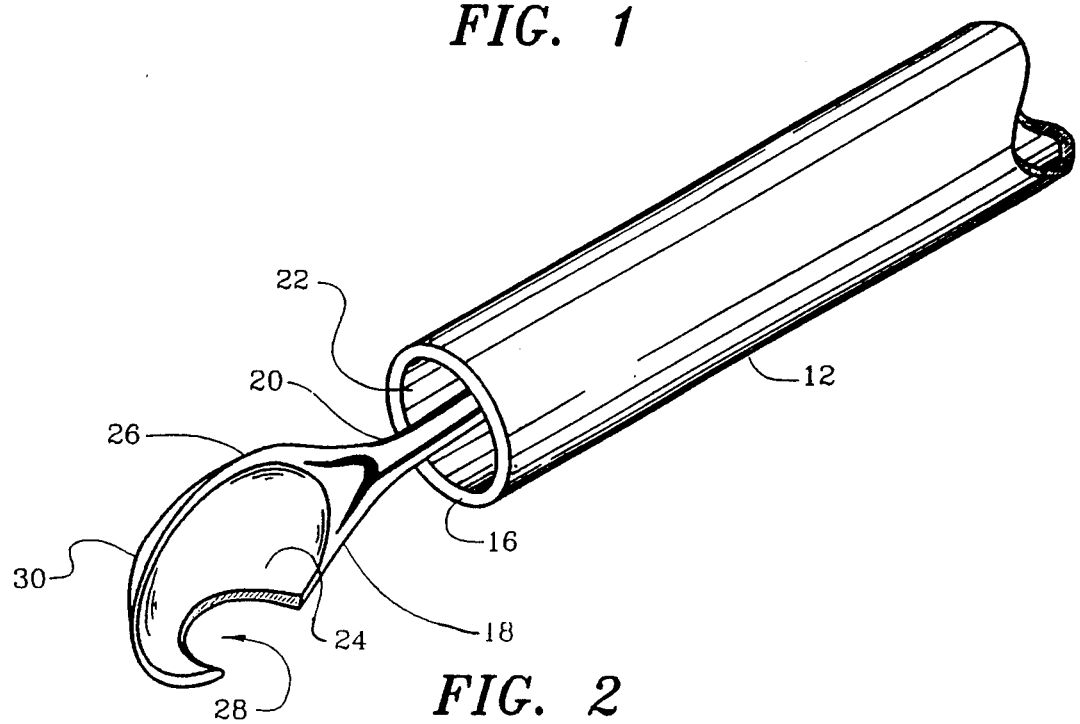
FIG. 1 is a perspective view of the distal end with electrode of the instant invention.

With reference to the several views of the drawings, there is depicted an improved laparoscopic cholecystectomy instrument generally characterized by reference numeral 10 which comprises a housing enclosure 12, a base end 14, and a distal end 16 respectively.

Figure 2:
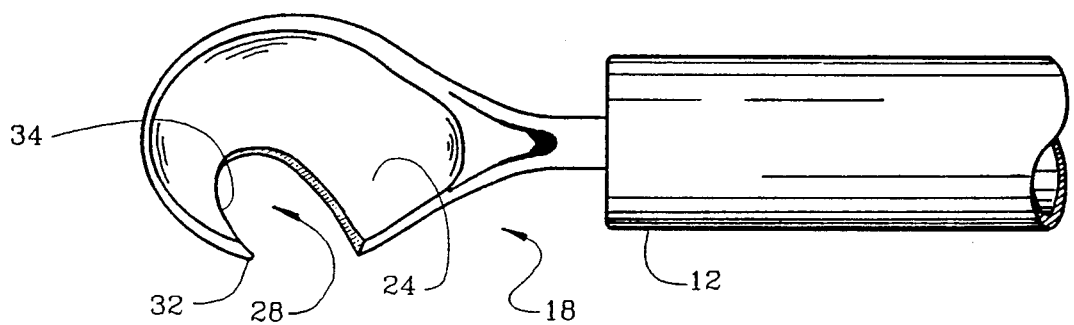
FIG. 2 is a side plan view of the distal end illustrated in FIG. 1.
Figure 3:
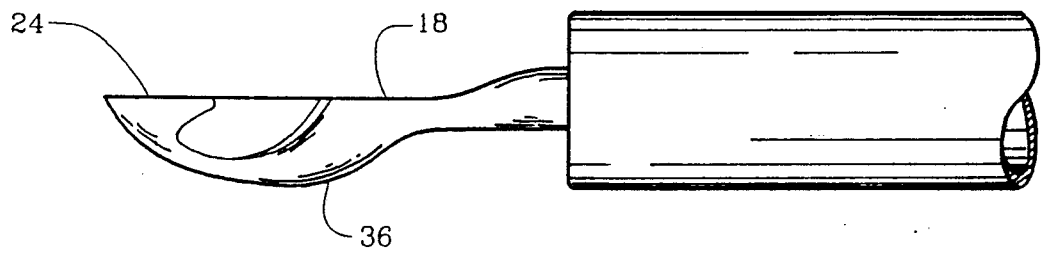
FIG. 3 is an top plan view of the distal end illustrated in FIG. 1.

In the preferred embodiment shown in FIGS. 1-3, the housing 12 is shown wherein electrode 18 extends obliquely from distal end 16. The housing 12 is constructed of stainless steel and TEFLON shrink wrap insulation. An insulated electrode connector 20 extends into the stainless steel tube housing 12 and is attached to a portion of the inner surface 22 of the housing 12 or alternatively may be formed integral with said housing during the plastic extruding process. When formed integral with the housing, the housing inner wall forms the required insulator. The interior chamber formed longitudinal within the housing allows for suction/irrigation functionality as described later in this specification.

The electrode 18 is characterized as a spoon shaped spatula defined by a centrally disposed concavity 24 having an outer circular perimeter 26 with a arcuate notch 28 placed therein. The tip 30 of the perimeter 26 is designed to extend past the insulation located at the end of a cannula. The spatula conforming to the gallbladder bed and the tip 30 used for bluntly dissecting the gallbladder from the liver. The notch 28 has an inward shaped hook that is used to ligate the cystic duct and cystic artery. Applying energy through the surgical tool assists in coagulation and cauterizing.

FIG. 2 is a top plan view of the instrument depicting the perimeter 26 of the electrode 18 having a similar width to housing 12 which is between ⅛ inch and 3/16 inch D diameter. The electrode 18 should be coated with a non-stick material, such as a thin coating of TEFLON insulation in order to prevent unwanted charring and tissue build up. The major surface area of the electrode 18 is defined by the upper concavity surface 24 which will support the gallbladder as a spoon. The notch 28 is sized small enough to allow gallbladder bridging between the upper concavity surface 24 and tip 32 yet the notch opening is large enough to encompass tissues to be dissected wherein the inner edge 34 is slightly chamfered for retracting dissection.

FIG. 3 is a side view of the electrode illustrating the lower concavity surface 36 parallel with the outer circumference of the housing allowing for the slidable insertion of the electrode through a cannula. The notch 28 extending proximately to the center of the concavity surface 24 and is disposed non-collinearly with the interior chamber allowing uninhibited fluid transfer within the housing 18.

FIG. 4 illustrates the attachment of housing 12 to the base 14. Base 14 includes a means for coupling to a laparoscopic instrument control valve which in this embodiment is threaded portion 42 with 0-ring seal 44, the means for coupling includes a centrally disposed aperture which forms a part of the interior chamber that extends longitudinally through the base 14 and housing 12 fluidly communicating with the distal end opening 22. A conductor 46 is placed perpendicular to the base end 14 for coupling to an external energy source for accepting the requisite heat energy for electrocautery for coagulating and cauterizing by an insulated direct electrical coupling to the electrode 18. The length of the housing 12 is between 11 inches and 15 inches permitting the electrode to reach the gallbladder when the instrument is inserted through the cannula.

Now referring to FIG. 5, the instrument of the instant device is shown attached to a NDHD Trumpet Valve 48 which controls the irrigation and suction of fluids through the housing by operation of the appropriate valve 50 or 52. The Trumpet Valve 48 permits the instrument to be readily gripped for manipulation of the electrode 18 formed into the spatula/hook combination relative to the tissue to be dissected.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. An electrode-surgical laparoscopic cholecystectomy instrument comprising: a housing means comprised of an elongated rigid tube having a distal end and a base end, said base end having a means for coupling to a laparoscopic instrument control valve; a conductor placed in said base end of said housing means for coupling to an external energy source; and an electrode extending outward from said distal end and mounted thereto, said electrode having a spoon shaped spatula surface at a first end, the spoon shaped spatula surface defined by a centrally disposed concavity having an outer circular perimeter with an arcuate notch placed therein, said notch defining a hook edge within the spoon shaped spatula surface, said electrode electrically connected to said conductor.

2. The laparoscopic cholecystectomy instrument according to claim 1, wherein said housing means is further defined as having a length and a diameter allowing for slidable insertion of said instrument into and extension therethrough of a cannula.

3. The laparoscopic cholecystectomy instrument according to claim 2, wherein said length of said housing means is greater than 11 inches.

4. The laparoscopic cholecystectomy instrument according to claim 2, wherein said diameter of said housing means is about 5/32 inches.

5. The laparoscopic cholecystectomy instrument according to claim 1, wherein said housing means is constructed of stainless steel coated with a TEFLON shrink wrap insulation.

6. The laparoscopic cholecystectomy instrument according to claim 1, wherein said laparoscopic instrument control valve is coupled to a vacuum source.

7. The laparoscopic cholecystectomy instrument according to claim 1, wherein the laparoscopic instrument control valve is a NEZHAT-DORSEY HYDRO-DISSECTION Trumpet Valve.

8. The laparoscopic cholecystectomy instrument according to claim 1, wherein the notch placed in the spoon shaped spatula surface of said electrode is disposed non-collinearly with said interior chamber allowing uninhibited fluid transfer with said housing means.

9. An electro-surgical laparoscopic cholecystectomy instrument comprising: a housing means comprised on an elongated stainless steel rigid tube coated with a TEFLON and shrink wrap insulation said rigid tube having a distal end and a base end having a length and a diameter allowing for slidable insertion of an electrode and extending through said rigid tube and, said base end having a means for coupling to a vacuum source; a conductor placed in said base end of said housing means for coupling to an external energy source; and said electrode extending outward from said distal end and mounted thereto, said electrode having a spoon shaped spatula surface at a first end, the spoon shaped spatula surface defined by a centrally disposed concavity having an outer circular perimeter with an arcuate notch placed therein, said electrode electrically connected to said conductor.

* * * * *

UNITED STATES PATENT AND TRADEMARK OFFICE
CERTIFICATE OF CORRECTION

PATENT NO. : 5,261,905
DATED : November 16, 1993
INVENTOR(S) : James H. Dorsey, III It is certified that error appears in the above-indentified patent and that said Letters Patent is hereby corrected as shown below:

On the Title page, item [75], inventor, change "Doresey" to -- Dorsey --.

Signed and Sealed this

Seventeenth Day of May, 1994

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,261,905
DATED : November 16, 1993
INVENTOR(S) : James H. Dorsey

It is certified that error appears in the above-indentified patent and that said Letters Patent is hereby corrected as shown below:

On the title page, under item [19] and item [76], change "Doresey" to --Dorsey--.

Signed and Sealed this

Twenty-first Day of June, 1994

Attest:

BRUCE LEHMAN

*Attesting Officer*          *Commissioner of Patents and Trademarks*